(12) United States Patent
DeMore et al.

(10) Patent No.: US 11,253,167 B2
(45) Date of Patent: Feb. 22, 2022

(54) METAL CLIP DETECTORS AND METHODS OF DETECTION

(71) Applicants: MUSC FOUNDATION FOR RESEARCH DEVELOPMENT, Charleston, SC (US); CLEMSON UNIVERSITY RESEARCH FOUNDATION, Clemson, SC (US)

(72) Inventors: Nancy DeMore, Charleston, SC (US); Delphine Dean, Central, SC (US); Scott R. Slaney, Seneca, SC (US); Melissa McCullough, Clemson, SC (US); Cody Jordan, Greer, SC (US); Joseph R. Wilson, III, Duncan, SC (US)

(73) Assignees: MUSC Foundation for Research Development, Charleston, SC (US); Clemson University Research Foundation, Clemson, SC (US)

( * ) Notice: Subject to any disclaimer, the term of this patent is extended or adjusted under 35 U.S.C. 154(b) by 313 days.

(21) Appl. No.: 16/328,430

(22) PCT Filed: Aug. 28, 2017

(86) PCT No.: PCT/US2017/048909
§ 371 (c)(1),
(2) Date: Feb. 26, 2019

(87) PCT Pub. No.: WO2018/039672
PCT Pub. Date: Mar. 1, 2018

(65) Prior Publication Data
US 2019/0269347 A1 Sep. 5, 2019

Related U.S. Application Data

(60) Provisional application No. 62/379,883, filed on Aug. 26, 2016.

(51) Int. Cl.
| | | |
|---|---|---|
| *A61B 5/06* | (2006.01) | |
| *A61B 90/00* | (2016.01) | |
| *A61B 5/05* | (2021.01) | |

(52) U.S. Cl.
CPC ............ *A61B 5/062* (2013.01); *A61B 5/05* (2013.01); *A61B 5/064* (2013.01); *A61B 90/39* (2016.02);
(Continued)

(58) Field of Classification Search
CPC ... A61B 5/061–064; A61B 5/05; A61B 90/39; A61B 2562/0223
See application file for complete search history.

(56) References Cited

U.S. PATENT DOCUMENTS

| | | | | |
|---|---|---|---|---|
| 5,005,592 A | * | 4/1991 | Cartmell | ............ A61B 5/06 128/899 |
| 7,787,931 B2 | | 10/2010 | Fabian et al. | |

(Continued)

FOREIGN PATENT DOCUMENTS

| | | | | |
|---|---|---|---|---|
| WO | 97/45157 A1 | 12/1997 | | |
| WO | WO-9902098 A1 | * 1/1999 | ............ | A61B 90/39 |

(Continued)

OTHER PUBLICATIONS

Canadian Office Action dated Feb. 4, 2020 in CA App. 3034561; 6 pages.

(Continued)

*Primary Examiner* — Sean D Mattson
(74) *Attorney, Agent, or Firm* — Perkins Coie LLP

(57) ABSTRACT

Systems and methods for detecting metal clips inserted within a portion of a body of a patient are disclosed herein. In one embodiment, a clip detector assembly includes a detector having a ferrous member, a transmitting coil around the ferrous member and configured to induce a current in the (Continued)

metal clip, and a receiving coil around the ferrous member and configured to receive a magnetic field generated by the current induced in the metal clip. The assembly can further include a control circuit having a band-pass filter configured to pass electrical signals induced by the magnetic field from the receiving coil that are within at most 35 kHz of a resonance frequency of the metal clip. The assembly still further includes a user notification component configured to alert a user to a location of the metal clip.

11 Claims, 10 Drawing Sheets

(52) U.S. Cl.
CPC ............... *A61B 2090/3908* (2016.02); *A61B 2090/3954* (2016.02); *A61B 2090/3991* (2016.02); *A61B 2562/0223* (2013.01)

(56) References Cited

U.S. PATENT DOCUMENTS

| | | | |
|---|---|---|---|
| 2006/0241397 A1* | 10/2006 | Govari | A61B 5/062 600/424 |
| 2006/0276686 A1 | 12/2006 | Tsuji et al. | |
| 2007/0249896 A1* | 10/2007 | Goldfarb | A61B 1/0051 600/101 |
| 2007/0265491 A1 | 11/2007 | Krag et al. | |
| 2008/0097199 A1* | 4/2008 | Mullen | A61B 90/39 600/431 |
| 2008/0228072 A1* | 9/2008 | Nycz | A61B 8/0833 600/437 |
| 2008/0294036 A1* | 11/2008 | Hoi | A61B 5/062 600/424 |
| 2015/0008914 A1* | 1/2015 | Hartwig | G01N 27/72 324/252 |

FOREIGN PATENT DOCUMENTS

| | | |
|---|---|---|
| WO | 2006022786 A1 | 3/2006 |
| WO | 2014/140566 A1 | 9/2014 |
| WO | 2014140566 A1 | 9/2014 |

OTHER PUBLICATIONS

Extended EP search report dated Apr. 9, 2020 for EP App. 17844562.3; 9 pages.

EP Communication dated Apr. 29, 2020 for EP App. 17844562.3; 1 page.

International Search Report and Written Opinion dated Dec. 13, 2017 in International Application No. PCT/US2017/048909, 13 pages.

Examiner's Report dated Nov. 12, 2020 in Canadian Patent Application No. 3,034,561, 6 pages.

* cited by examiner

METAL CLIP DETECTORS AND METHODS OF DETECTION

CROSS-REFERENCE TO RELATED APPLICATION(S)

The present application is a National Phase application of International Application No. PCT/US17/48909, filed Aug. 28, 2017, which claims priority to U.S. Provisional Application No. 62/379,883, filed Aug. 26, 2016, both of which are incorporated herein by reference in their entireties.

TECHNICAL FIELD

The present technology relates generally to devices, systems, and methods for detecting clips or other metal objects inserted into a patient. In particular, some embodiments of the present technology relate to a clip detector configured for external use to generally locate a clip within a patient's body, and for internal use within an incision in the patient to more particularly locate the clip.

BACKGROUND

Metal clips (e.g., titanium clips) are used to identify tumors found, for example, via radiographic imaging in order to later identify tissue to be removed during surgery. When a patient has an abnormal mammogram, a stereotactic or ultrasound guided core breast biopsy is performed and a clip is placed at the biopsy site. A biopsy site may be marked with a clip in order to later identify the tissue region from which the biopsy was taken, for example, if a determination is made that additional tissue needs to be removed. In some instances, the clip, a reflective chip, a radioactive marker, and/or another fiducial marker is placed in a lesion (e.g., a tumor) at the time of biopsy, prior to neoadjuvant chemotherapy, radiation, or surgical removal of the lesion. If, for example, there is a complete radiographic response, the clip may be used intraoperatively to remove the tissue around the clip. Similar procedures may be used for cancers of the rectum, liver, and esophagus, or for other procedures such as sentinel node biopsies.

In order to remove the additional tissue via surgery, the patient has a surgical localization procedure so that the clip may be easily located later during surgery. This surgical localization procedure is typically performed outside of the operating room in a radiology department. During the surgical localization procedure, a wire is placed adjacent to the site of the clip, to later guide the surgeon to the clip in the operating room.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

Figure 1:
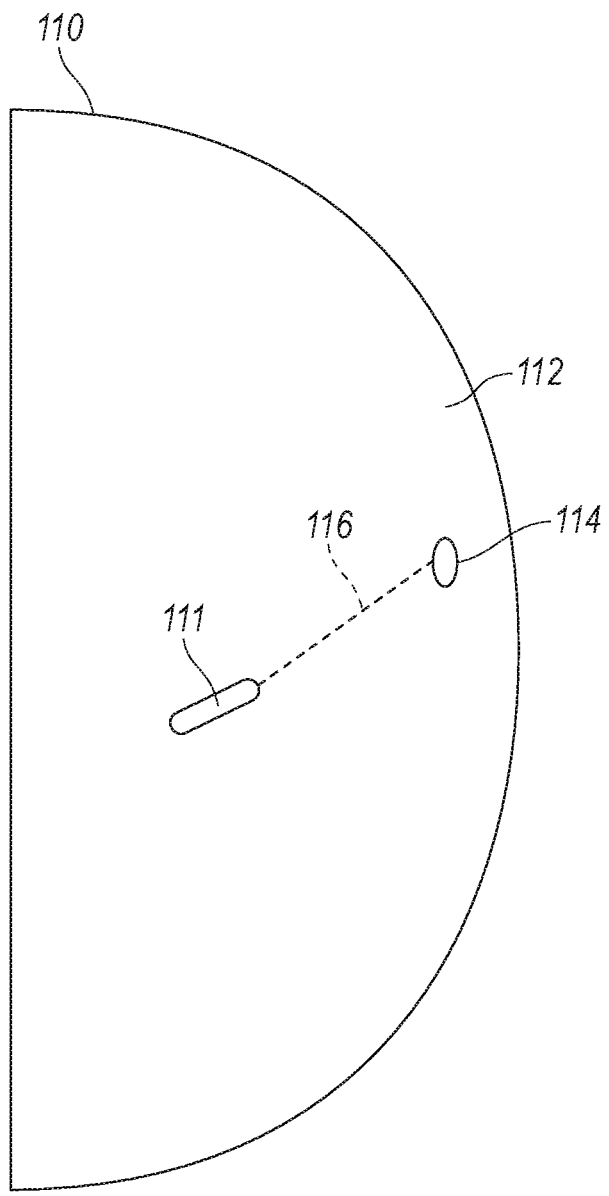
FIG. 1 is a schematic view of a portion of a patient's body with a metal clip inserted therein.

Aspects of the present disclosure are directed generally toward devices for detecting metal clips within a patient (e.g., at a biopsy site within a human patient) and associated methods. Because conventional clip localization procedures are performed separately, outside of the operating room and prior to surgery, patients and doctors experience scheduling conflicts and inefficiencies. The very design aspect of metal (e.g., titanium) clips that make them ideal for placement during biopsy also make locating these clips during surgery a challenge. Specifically, while the ferromagnetic properties of titanium clips are advantageous in that patients with titanium clips may be safely examined with magnetic resonance imaging (MRI), these same ferromagnetic properties also greatly reduce the sensitivities of devices such as metal detectors. Additionally, while metal detectors, such as very low frequency metal detectors, are known, these metal detectors are relatively large and are not configured to work within the confines of a skin incision. The devices and methods described herein provide for detection of titanium or other metal clips without reliance on devices, such as ultrasound machines, that are typically used to locate such clips prior to surgery.

In several of the embodiments described below, a system for detecting a metal clip within a patient includes at least one detector having a ferrous core, a receiving coil wrapped around a first portion of the ferrous core, and a transmitting coil wrapped around a second portion of the ferrous core and the receiving coil. The transmitting coil is coupled to a power source and configured to induce a current in the metal clip, while the receiving coil is configured to receive a magnetic field generated by the current induced in the metal clip. The assembly can further include a control circuit having a band-pass filter configured to pass, from the receiving coil, certain electrical signals induced by the magnetic field in the receiving coil. In certain embodiments, the band-pass filter only passes electrical signals that are within at most 35 kHz of a resonance frequency of the metal clip. In some embodiments, the assembly can also include a user notification component configured to receive the electrical signals passed by the band-pass filter and alert a user to a location of the metal clip. In certain embodiments, the detector is at least partially insertable within the patient.

In the following detailed description, specific details are set forth to provide an understanding of the present technology. However, the present technology may be practiced without some of these specific details. In some instances, well-known structures and techniques have not been shown in detail so as not to obscure the present technology. The terminology used in the description presented below is intended to be interpreted in its broadest reasonable manner, even though it is being used in conjunction with a detailed description of certain specific embodiments of the disclosure. Certain terms may even be emphasized below; however, any terminology intended to be interpreted in any restricted manner will be overtly and specifically defined as such in this Detailed Description section.

FIG. 1 is a schematic view of a portion 110 of a patient's body, with a clip 111 disposed therein. The clip 111 is a metal clip that may be inserted into tissue, such as breast, rectal, liver or esophageal tissue, during a biopsy procedure. In some embodiments, the clip 111 is made of titanium, nitinol, stainless steel, and/or other suitable metals. More specifically, the clip 111 may be a titanium biopsy site marker sold under the trademark SECURMARK by Hologic, Inc., which is used for stereotactic biopsies, or any of the various breast tissue markers sold under the trademark UltraClip by Bard Peripheral Vascular, Inc., which are used for ultrasound guided breast biopsies. In some embodiments, the portion 110 is a portion of a breast of the patient while, in other embodiments, the portion 110 can be a portion of the rectum, liver, esophagus, or other portion of the patient's tissue, organs, etc. As illustrated in the embodiment of FIG. 1, the portion 110 includes a skin surface 112 (e.g., a skin surface of a breast of the patient). In certain embodiments, once a general location of the clip 111 within the portion 110 of the patient's body is determined, an incision 114 is made through the skin surface 112 to allow for removal of the clip 111 (e.g., along an incision path 116). As described in further detail below, a more exact location of the clip 111 within the portion 110 of the patient's body can be determined using one or more detectors that are inserted into the incision 114. For the sake of illustration, some of the features of the embodiments described below with reference to FIGS. 2-9 are described in the context of the embodiment of FIG. 1.

Figure 2:
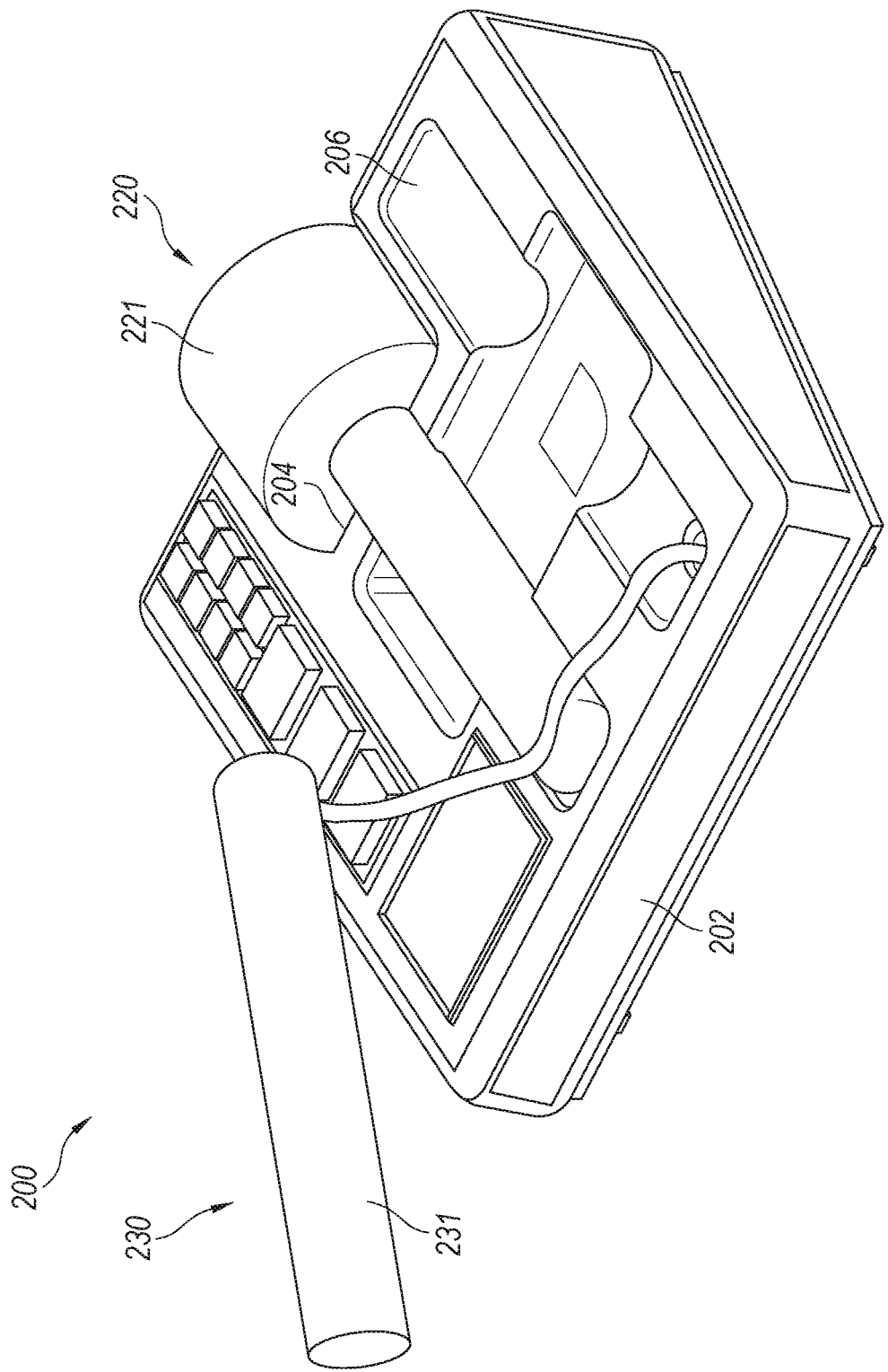
FIG. 2 is an isometric view of a clip detector assembly configured in accordance with embodiments of the present technology.

FIG. 2 is an isometric view of a clip detector assembly 200 configured in accordance with the present technology. The clip detector assembly 200 includes a first detector 220 and a second detector 230 (collectively "detectors 220, 230") that may be disposed in a base 202. In some embodiments, the base 202 includes a first portion 204 and a second portion 206 configured (e.g., shaped) to receive the detectors 220, 230. For example, in certain embodiments the detectors 220, 230 can be snugly positioned within the first and second portions 204, 206 of the base 202, respectively, while not in use. In FIG. 2, the second detector 230 is shown removed from the second portion 206 of the base 202, while the first detector 220 is positioned within the first portion 204.

In general, the first detector 220 has a larger diameter than second detector 230 and may be used to scan (e.g. pass over) the skin surface 112 of the portion 110 of the patient's body to determine a general location of the clip 111 within the portion 110. When the portion 110 does not include a skin surface (e.g., when the portion 110 is an internal organ or other internal portion of the patient), the first detector can scan a region proximate the portion 110 to determine the general location of the clip 111. After determining a general location of the clip 111, the second detector 230 may then be inserted into the portion 110 via the incision 114 and used to probe the incision 114 to determine a more exact location of the clip 111.

As shown in FIG. 2, the first detector 220 has a first outer casing 221 and the second detector 230 has a second outer casing 231 (collectively "outer casings 221, 231"). The outer casings 221, 231 may have a thickness of about 1-5 mm, such as a 1 mm, 2 mm, 3 mm, 4 mm, or 5 mm thickness. In some embodiments, the thicknesses of the outer casings 221, 231 are the same while, in other embodiments, the thickness of the outer casings 221, 231 can differ. The first outer casing can have a diameter of about 20-80 mm (e.g., about 30-75 mm, about 40-50 mm, etc.) and a total length of about 100-200 mm (e.g., about 120-180 mm, about 160-170 mm, etc.). The first outer casing 221 also defines an inner cavity (e.g., as illustrated in the partially cross-sectional view of FIG. 3) having a length of about 95-195 mm (e.g., about 100 to 150 mm). The second outer casing 231 has a smaller diameter relative to the first outer casing 221 so as to enable probing of the portion 110 of the patient's body (e.g., via the incision 114) with minimal damage to the tissue. For example, the second outer casing 231 can have a diameter of about 10-25 mm (e.g., about 12-20 mm, about 12-18 mm, etc.) and can be sized to fit through, for example, cosmetically acceptable incisions. The second outer casing 231 can have a total length of about 100-200 mm (e.g., about 120-180 mm, about 160-170 mm, etc.), and defines an inner cavity having a length of about 95-195 mm (e.g., about 100 to 150 mm).

The outer casings 221, 231 may be waterproof and may be made out of a polymer, such as polyvinyl alcohol (PVA), nylon, acrylate polymer, or some combination thereof. Portions of the outer casings 221, 231 that come into contact with the patient are preferably biocompatible so as to, for example, enable probing of the portion 110 of the patient's body to locate the clip 111. In some embodiments, the second outer casing 231 may include a protective cover to facilitate sterilization between uses. For example, the protective cover may be a medical condom or a hard plastic disposable sheath.

Figure 3:
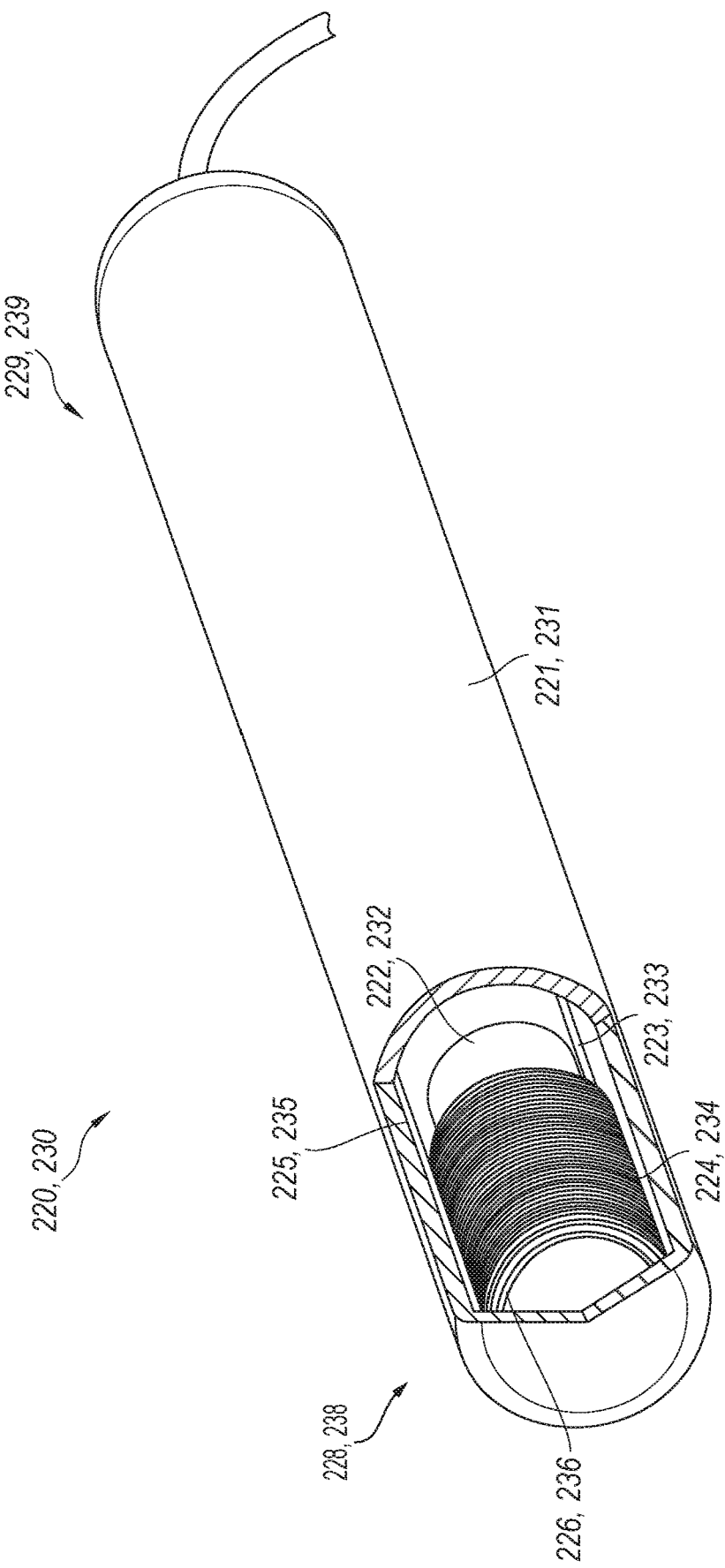
FIG. 3 is a partially cross-sectional, isometric view of a clip detector configured in accordance with embodiments of the present technology.

FIG. 3 is a partially cross-sectional, isometric view of a detector configured in accordance with embodiments of the present technology. In particular, the detector shown in FIG. 3 is representative of any of the detectors disclosed herein, which have similar components. For example, the detector illustrated in FIG. 3 can be either of the detectors 220, 230 described with reference to FIG. 2 and, accordingly, reference is made to both detectors 220, 230 in the description of FIG. 3. In FIG. 3, the outer casing (e.g., the first outer casing 221 or second outer casing 231) of the illustrated detector has been cut away to illustrate internal components of the detector.

In general, the detector illustrated in FIG. 3 has a ferrous member (e.g., a ferrous core), a transmitting coil, and a receiving coil. For example, the first detector 220 has a first ferrous member 222, a first transmitting coil 224, and a first receiving coil 226. Similarly, the second detector 230 has a second ferrous member 232, a second transmitting coil 234, and a second receiving coil 236. The first and second transmitting coils 224, 234 (collectively "transmitting coils 224, 234") are powered via first and second leads 223, 233, respectively. Likewise, the first and second receiving coils 226, 236 (collectively "receiving coils 226, 236") are coupled to (e.g., powered via) first and second leads 225, 235, respectively. The first and second ferrous members 222, 232 (collectively "ferrous members 222, 232") may be solid members that include ferrous material with a high magnetic permeability. In other embodiments, the ferrous members 222, 232 can be made out of other suitable materials. Moreover, as illustrated in the embodiment of FIG. 3, the ferrous members 222, 232, transmitting coils 224, 234, and receiving coils 226, 236 are located within a distal portion 228, 238 of the detectors 230, 240, respectively. In other embodiments, some or all of these components may be located at least partially in another portion of the detectors 220, 230, such as in a proximal portion 229, 239 of the detectors 220, 230, respectively.

Each of the detectors 220, 230 is configured to generate (e.g., produce) and receive (e.g., detect) magnetic fields. While the detectors 220, 230 have similar basic components, the functionality of those components varies based on certain parameters that, for example, determine the size, shape, and/or strength of the magnetic field generated by each detector. For example, in the embodiment illustrated in FIG. 2, the first detector 220 has a larger diameter than the second detector 230, which can provide space for a larger first transmitting coil 224, first receiving coil 226, and/or first ferrous member 222 (as compared to the corresponding components of the second detector 230). Accordingly, the first detector 220 can generate and/or detect a magnetic field with different characteristics than the second detector 230.

Figure 4A:
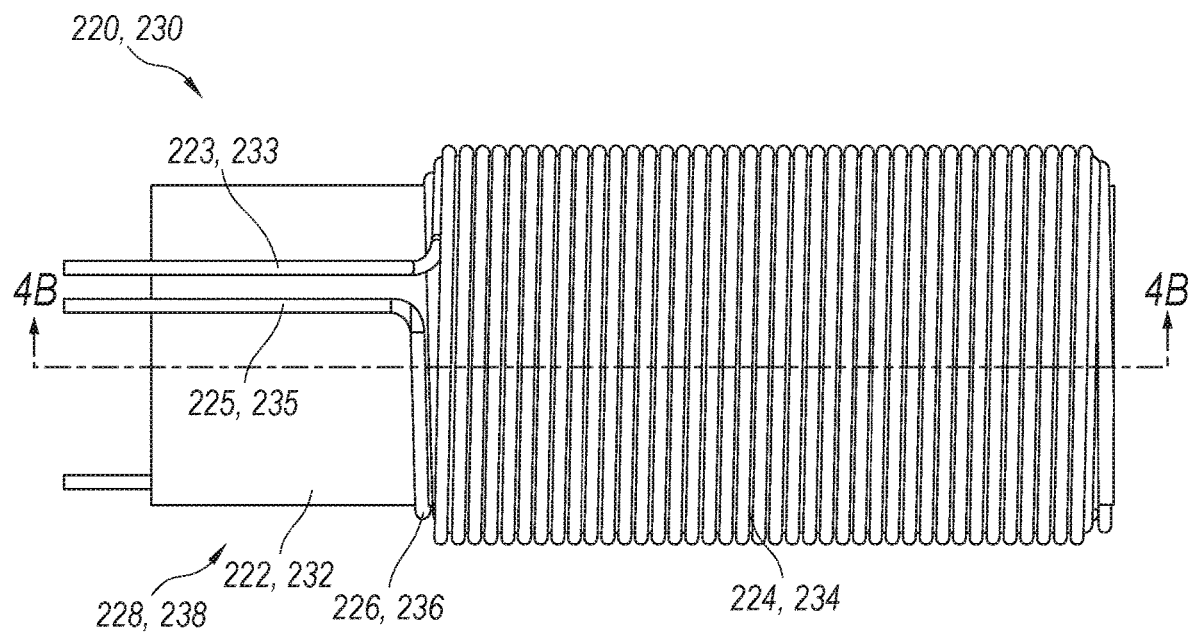
FIG. 4A is a side view of a distal portion of the clip detector shown in FIG. 3.
Figure 4B:
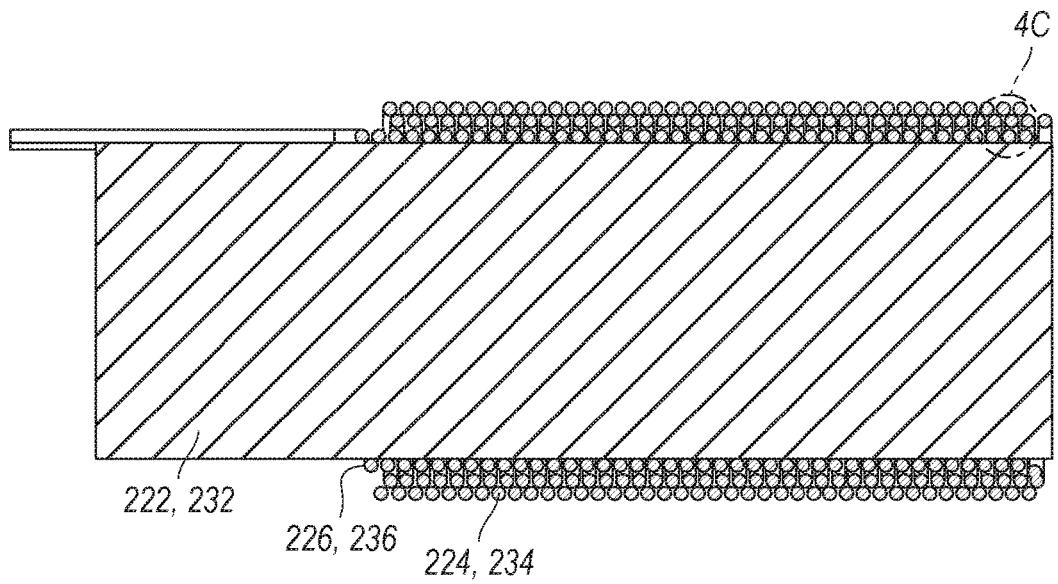
FIG. 4B is a side-cross sectional view of the distal portion of the clip detector shown in FIG. 4A.
Figure 4C:
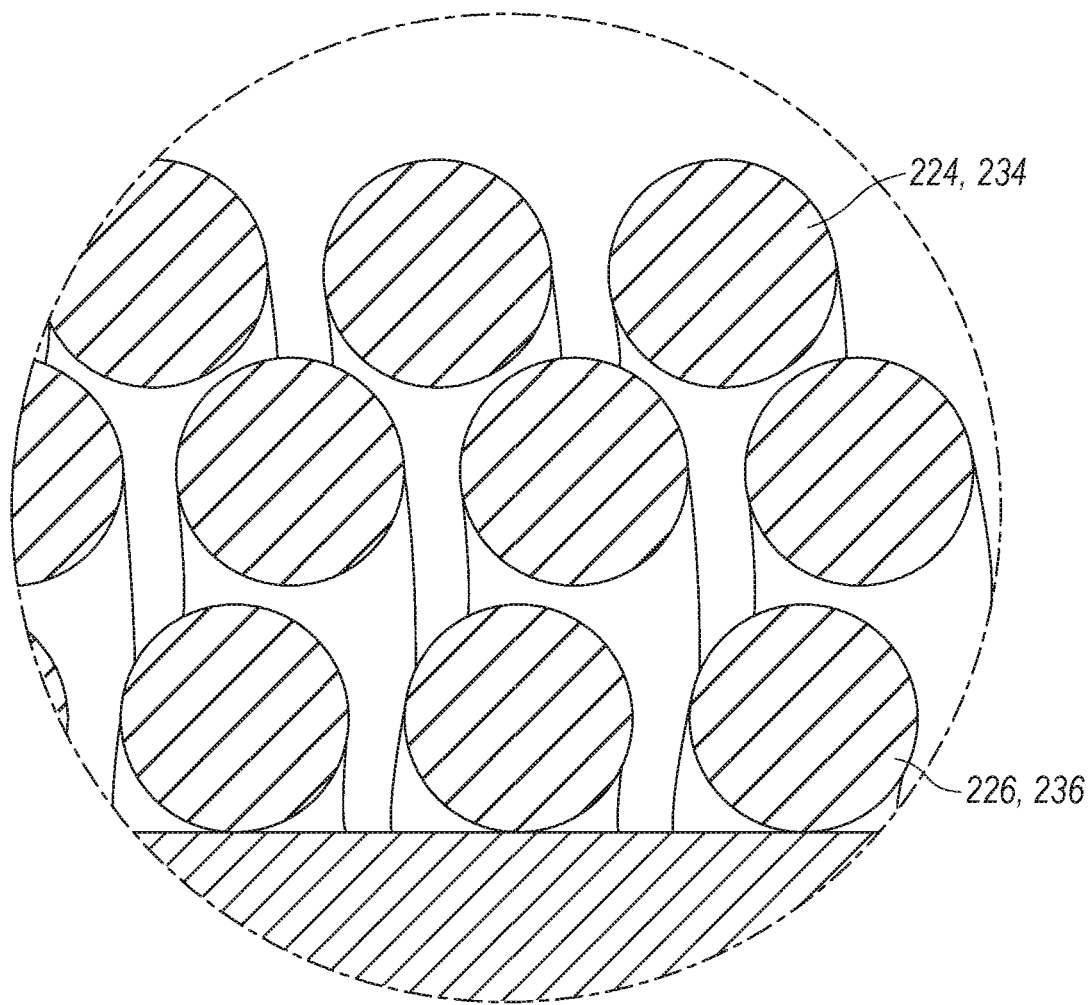
FIG. 4C is an enlarged view of a portion of the clip detector illustrated in FIG. 4B.

FIG. 4A is a side view of a distal portion of the detector shown in FIG. 3 (e.g., the distal portions 228, 238 of the detectors 220, 230, respectively), with the outer casing removed for clarity of illustration. FIG. 4B is a side cross-sectional view of the distal portion of the detector shown in FIG. 4A. FIG. 4C is an enlarged view of a portion of the detector illustrated in FIG. 4B. Referring to FIGS. 4A-4C together, the transmitting coils 224, 234 of the detectors 220, 230 may be wrapped around (e.g., positioned radially around) the receiving coils 226, 236, respectively. Similarly, the receiving coils 226, 236 can be wrapped around the ferrous members 222, 232, respectively. That is, the receiving coils 226, 236 can be positioned radially inward (e.g., below) the transmitting coils 224, 234. In some embodiments, the transmitting coils 224, 234 and receiving coils 226, 236 are wrapped around the same portion of the ferrous members 222, 232 (e.g., having the same axial length and positioning) while, in other embodiments, the transmitting coils 224, 234 and receiving coils 226, 236 can have different configurations (e.g., having different axial lengths and/or positioning).

In some embodiments, the diameter of the first ferrous member 222 of the first detector 220 can be about 20-80 mm (e.g., about 30-75 mm, about 40-50 mm, etc.). In some embodiments, the first transmitting coil 224 of the first detector 220 may include 1-10 layers, such as 1 layer, 2 layers, 3 layers, 4 layers, 5 layers, 6 layers, 7 layers, 8 layers, 9 layers, or 10 layers. Each layer of the first transmitting coil 224 can include about 500-5000 turns (e.g., 500 turns, 600 turns, 700 turns, 800 turns, 900 turns, 1000 turns, etc.). The first transmitting coil 224 can have a length of about 20-50 mm (e.g., about 25-45 mm, about 30-40 mm, etc.). In certain embodiments, the first transmitting coil 224 may be configured to produce an inductance of about 1-10 mH. In some embodiments, passing about 0.25-2.5 A through the first transmitting coil 224 (e.g., via the lead 223) produces a magnetic field capable of inducing an opposing current in the clip 111 at a distance of about 1-20 cm (e.g., about 7.5-15 cm, about 5-10 cm, etc.

The first receiving coil 226 of the first detector 220 may include 1-10 layers, such as 1 layer, 2 layers, 3 layers, 4 layers, 5 layers, 6 layers, 7 layers, 8 layers, 9 layers, or 10 layers. Each layer of the first transmitting coil 224 can include about 500-5000 turns (e.g., 500 turns, 600 turns, 700 turns, 800 turns, 900 turns, 1000 turns, etc.). The first receiving coil 226 can have a length of about 20-50 mm (e.g., about 25-45 mm, about 30-40 mm, etc.). In some embodiments, the length of the first receiving coil 226 is the same as or substantially the same as the length of the first transmitting coil 224. In certain embodiments, the first receiving coil 226 can have an inductance of about 5-25 µH (e.g., about 15 µH). The first receiving coil 226 is configured to receive (e.g., detect) a magnetic field emanating from the clip 111. More particularly, the opposing current in the clip 111 generates a magnetic field that can be received by the first receiving coil 226 and that induces a current (i.e., electrical signals) in the first receiving coil 226. In some embodiments, the first receiving coil 226 is configured to detect a location of the clip 111 (e.g., have electrical signals induced in the first receiving coil 226) at a distance of about 1-20 cm e.g., about 7.5-15 cm, about 5-10 cm, etc.). That is, in some embodiments, the first receiving coil 226 can be configured to detect the clip 111 at about the same distance that the first transmitting coil 224 is configured to induce an opposing current in the clip 111.

The second detector 230 has a smaller diameter than the first detector 220 and its second transmitting coil 234, second receiving coil 236, and/or second ferrous member 232 can be correspondingly smaller. For example, the second ferrous member 232 can have a diameter of about 5-25 mm about 6-20 mm, about 8-12 mm, etc.). The second transmitting coil 234 may include 1-10 layers, such as 1 layer, 2 layers, 3 layers, 4 layers, 5 layers, 6 layers, 7 layers, 8 layers, 9 layers, or 10 layers. Each layer of the second transmitting coil 234 can include about 500-5000 turns, such as 1500 turns, 1600 turns, 1700 turns, 1800 turns, 1900 turns, 2000 turns, 2100 turns, 2200 turns, 2300 turns, 2400 turns, 2500 turns, etc. In some embodiments each layer of the second transmitting coil 234 has more turns than each layer of the first transmitting coil 224 of the first detector 220. The second transmitting coil 234 can have a length of about 20-50 mm (e.g., 25-45 mm, 30-40 mm, etc.). In certain embodiments, the second transmitting coil 234 may be configured to produce an inductance of 1-10 mH. In some embodiments, passing 0.25-2.5 A through the second transmitting coil 234 produces a smaller magnetic field relative to the magnetic field of the first detector 220. The magnetic field generated by the second transmitting coil 234 can induce an opposing current in the clip 111 at a distance of about 1-10 cm (e.g., about 2-4 cm, about 3-5 cm, etc.).

The second receiving coil 236 of the second detector 230 includes 1-10 layers, such as 1 layer, 2 layers, 3 layers, 4 layers, 5 layers, 6 layers, 7 layers, 8 layers, 9 layers, or 10 layers. Each layer of the second receiving coil 236 can include about 500-5000 turns, such as 1500 turns, 1600 turns, 1700 turns, 1800 turns, 1900 turns, 2000 turns, 2100 turns, 2200 turns, 2300 turns, 2400 turns, 2500 turns, etc. The second receiving coil 236 can have a length of about 20-50 mm (e.g., about 25-45 mm, about 30-40 mm, etc.). In some embodiments, the length of the second receiving coil 236 is the same or substantially the same as the length of the second transmitting coil 234. In certain embodiments, the second receiving coil 236 can have an inductance of about 5-25 µH (e.g., about 15 µH). The second receiving coil 236 is configured to receive a magnetic field emanating from the clip 111 that is generated by the opposing current induced in the clip 111 by the second transmitting coil 234. In some embodiments, the second receiving coil 236 is configured to detect a location of the clip 111 (e.g., have electrical signals induced in the second receiving coil 236) at a distance of about 1-10 cm (e.g., about 2-4 cm, about 3-5 cm, etc.). That is, in some embodiments, the second receiving coil 236 can be configured to detect the clip 111 at about the same distance as the second transmitting coil 234 is configured to induce an opposing current in the clip 111.

In general, the geometries of the detectors 220, 230 and/or other characteristics of the detectors 220, 230 (e.g., a resistance of the detectors 220, 230, a power supplied to the detectors 220, 230, etc.) can be varied to tune the detection characteristics (e.g., a detection range) of the detectors 220, 230. For example, increasing the power to the detectors 220, 230 can increase the size of the magnetic field generated by the detectors 220, 230, as well as the current induced in the clip 111. Accordingly, the magnetic field generated by the clip 111 may be easier to detect. Similarly, varying the geometries of the detectors can change the shape of the magnetic fields generated by the detectors 220, 230 to, for example, increase or decrease the depth the generated magnetic fields penetrate within the portion 110 of the patient's body.

Figure 5:
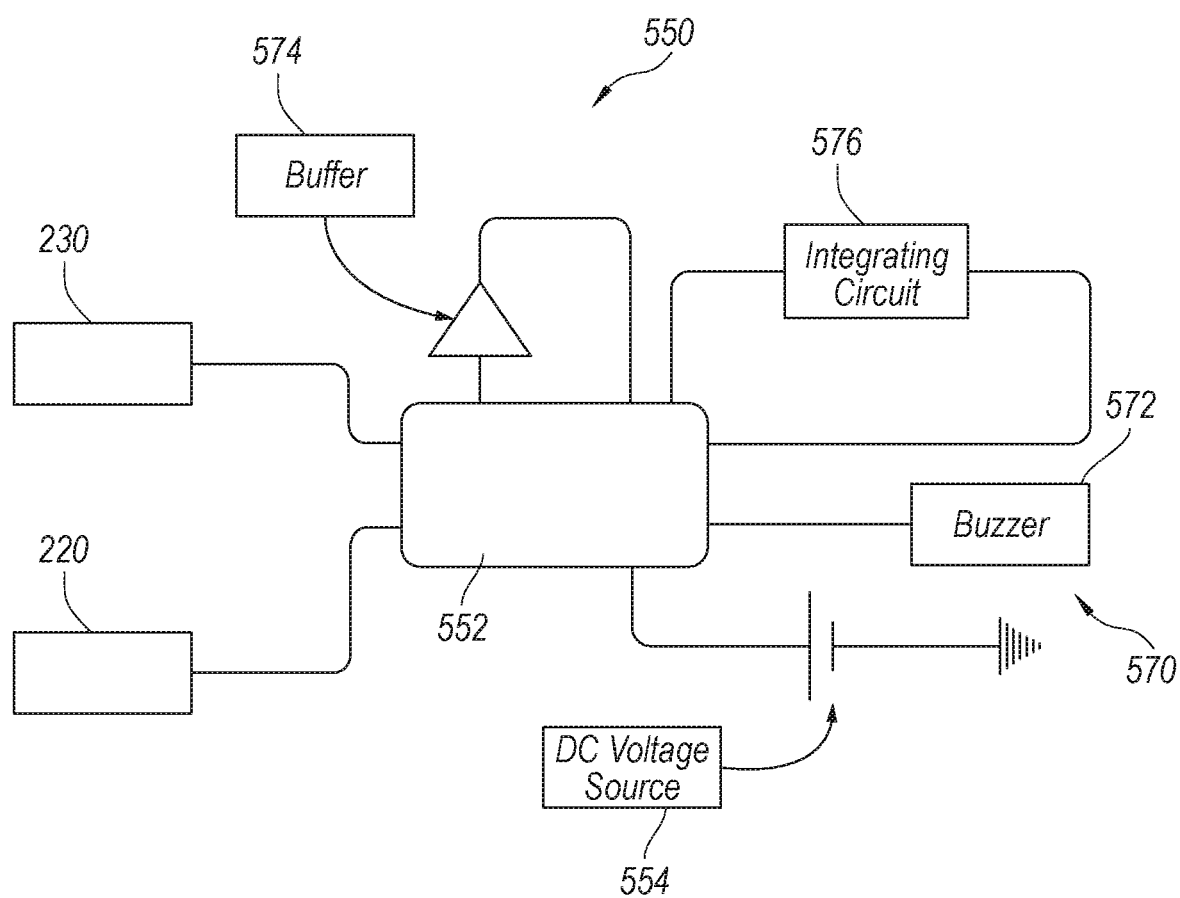
FIG. 5 is a schematic circuit diagram of the clip detector assembly shown in FIG. 2 in accordance with embodiments of the present technology.

FIG. 5 is a schematic circuit diagram of the clip detector assembly 200 shown in FIG. 2. In the embodiment illustrated in FIG. 5, the first detector 220 and the second detector 230 are electrically coupled to a control circuit 550 (e.g., via the first leads 223, 225 and second leads 233, 235, respectively). The control circuit 550 has a microcontroller 552 that controls power to the transmitting coils 224, 234 and also receives signals from the receiving coils 226, 236. The transmitting coils 224, 234 and/or receiving coils 226, 236 are powered by a power source 554 (e.g., mains or non-mains power source) that provides a DC voltage. In some embodiments, the power source 554 is a battery that may be disposed within the detectors 220, 230, or as part of the base 202 (FIG. 2). In certain embodiments, the power source 554 provides about 9 V to the clip detector assembly 200, of which about 5-9 V are provided to the detectors 220, 230. The control circuit 550 may also include a user notification component 570 that includes, for example, a buzzer 572 (e.g., a speaker) that, in combination with other elements of the control circuit 550 is configured to alert a user of the clip detector assembly 200 to a location of the clip 111. In some embodiments, the buzzer 572 can produce a higher pitch or a louder tone as the first detector 220 and/or second detector 230 are positioned closer to the clip 111. In certain embodiments, the user notification component 570 can include a graphical display that can, for example, display an approximate distance of the clip 111 from the first detector 220 and/or second detector 230. As further shown in FIG. 5, the control circuit 550 can further include one or more buffers 574, integrating circuits 576, and/or or other suitable components.

Figure 6A:
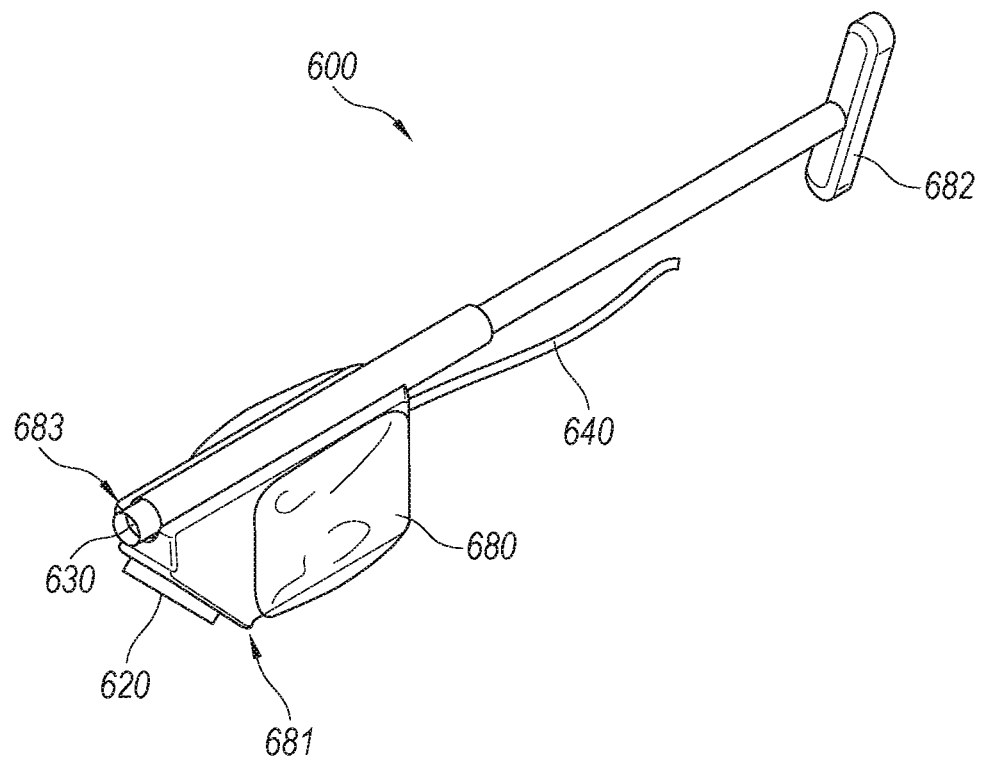
FIGS. 6A and 6B are isometric views of a clip detector assembly in a first position and a second position, respectively, in accordance with embodiments the present technology.
Figure 6B:
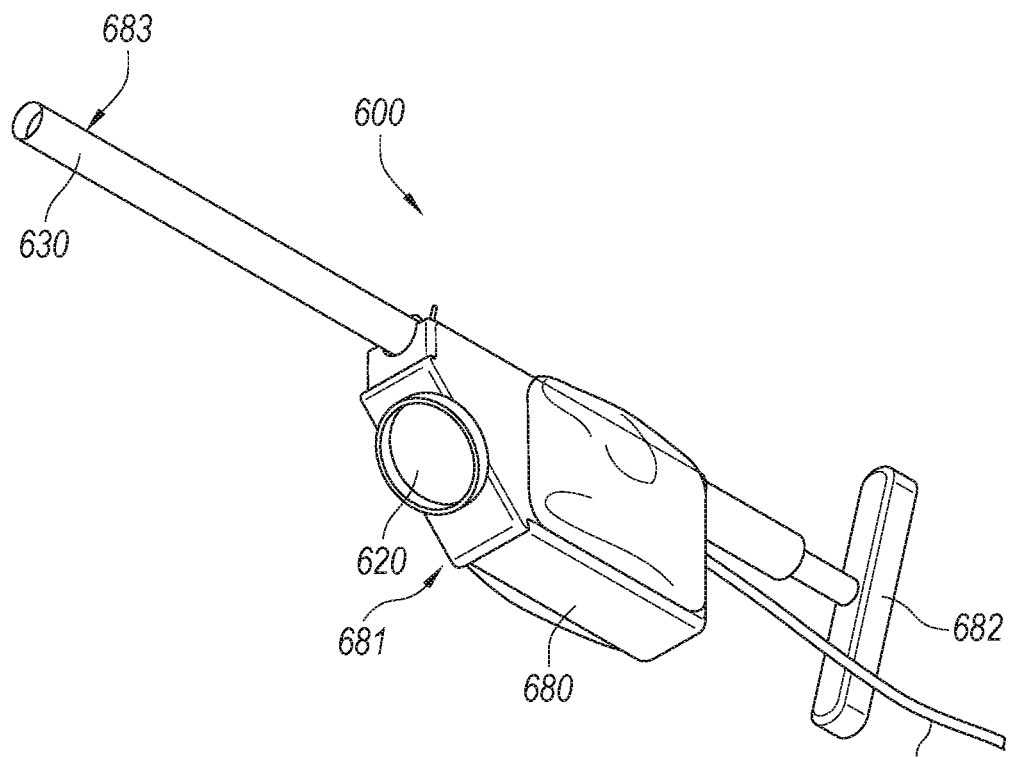

FIGS. 6A and 6B illustrate another embodiment of a clip detector assembly 600 in a first position and a second position, respectively, in accordance with the present technology. Referring to both FIGS. 6A and 6B together, the clip detector assembly 600 can include some features that are generally similar to those of the clip detector assembly 200 shown in FIG. 2B. For example, the clip detector assembly 600 includes a first detector 620 and a second detector 630 that can each have a receiving coil and a transmitting coil, and that can each be electrically coupled to a control circuit. The clip detector assembly 600 can further include a corded power source 640 or, in other embodiments, a battery or other power source for providing power to the first and second detectors 620, 630. In contrast to the clip detector assembly 200 (e.g., in lieu of the base 202), the clip detector assembly 600 includes a grip portion 680 and a plunger 682 slidably coupled to the grip portion 680 (e.g., to a top surface of the grip portion 680). The first detector 620 is disposed at a distal portion 681 of the grip portion 680, while the second detector 630 is disposed at a distal portion 683 of the plunger 682. Accordingly, the plunger 682 may be used to adjust the position of the second detector 630 relative to the first detector 620.

As illustrated in the embodiment of FIG. 6A, during operation, the clip detector assembly 600 may initially be in a first position with the plunger 682 pulled distally away from the grip portion 680 (e.g., in a retracted position). The first position enables the first 620 to be located close to the skin surface 112 of the portion 110 of the patient's body for, for example, generally locating the clip 111 during a scanning step. As illustrated in the embodiment of FIG. 6B, in the second position, the plunger 682 may be pushed proximally towards the grip portion 680 to extend the second detector 630 away from the grip portion 680. For example, once a general location of the clip 111 is determined using the first detector 620, the incision 114 may be made in the portion 110 of the patient's body. The second detector 630 may then be inserted into the incision 114 to determine a more exact location of the clip 111. In some embodiments, a user can grip the grip portion 680 and the plunger 682 and pull or push the two components relative to each other to transform the clip detector assembly 600 from the first position to the second position.

Figure 7:
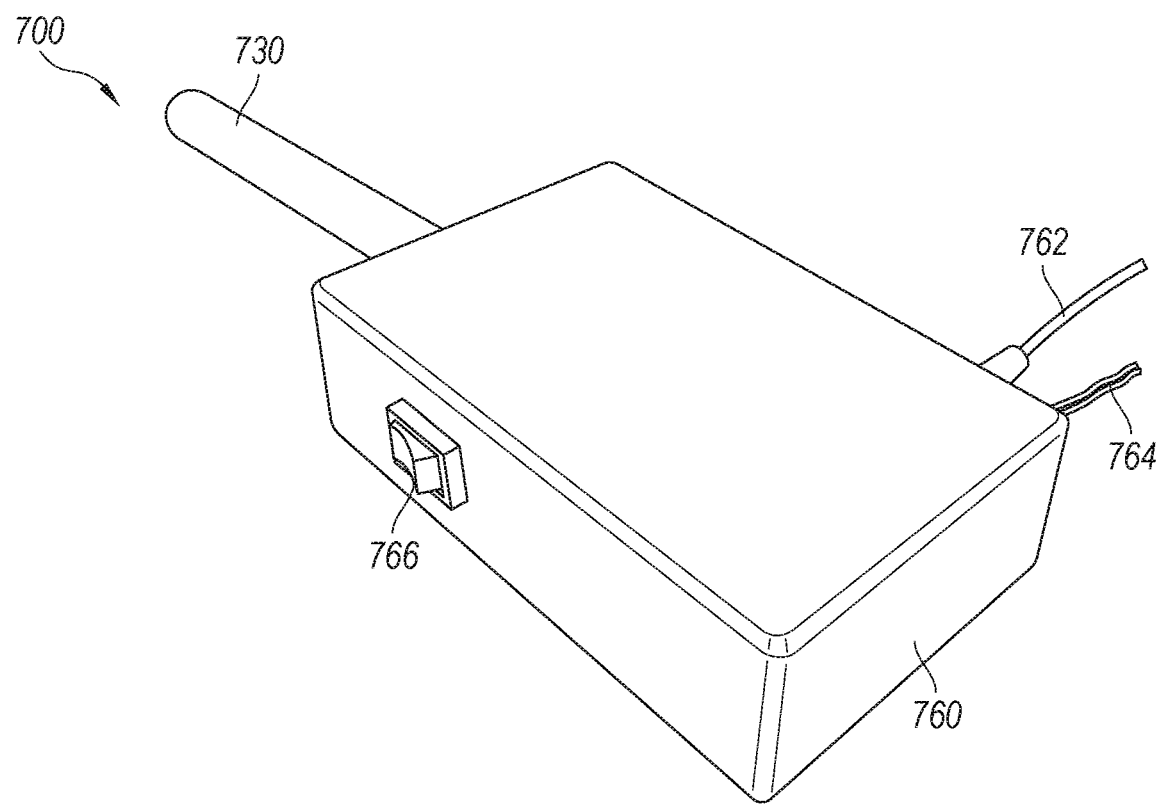
FIG. 7 is an isometric view of a clip detector assembly configured in accordance with another embodiment of the present technology.

Each of the embodiments described above with reference to FIGS. 2-6 include two detectors (e.g., having different detection and/or magnetic field generation characteristics). However, in other embodiments, a clip detector assembly according to the present technology may include only a single detector, or more than two detectors (e.g., multiple detectors with transmitting and/or receiving coils of different sizes). For example, FIG. 7 is an isometric view of a clip detector assembly 700 configured according to another embodiment of the present technology and having only a single detector 730. The detector 730 can include some features generally similar to the features of the detectors described with reference to FIGS. 3-4C. For example, the detector 730 can include (a) a ferrous member, (b) a transmitting coil wrapped around the ferrous member and configured to produce a magnetic field capable of inducing an opposing current in the clip 111, and (c) a receiving coil wrapped around the ferrous member and configured to receive (e.g., detect) a magnetic field emanating from the clip 111. In some embodiments, the transmitting coil is wrapped around the receiving coil. In certain embodiments, the detector 730 includes an outer casing having a diameter of less than about 25 mm (e.g., about 10-25 mm). The outer casing can be waterproof and made out of a polymer (e.g., polyvinyl alcohol (PVA), nylon, acrylate polymer, etc.), and is configured to enable probing of portion 110 of the patient's body via the incision 114 to locate the clip 111.

In some embodiments, the transmitting and receiving coils of the detector 730 are configured (e.g., sized, including a certain number of layers, adjustable, etc.) to induce an opposing current in the clip 111, and to detect a magnetic field emanating from the clip 111, over a wider range of distances than either of the detectors 220, 230 (FIGS. 2-4C). Accordingly, the detector 730 can function as both a scanning detector to detect a general location of the clip 111 within the portion 110 of the patient's body when the detector 730 is passed over the skin surface 112, and as an insertable detector that is insertable into the incision 114 for detecting a more exact location of the clip 111.

More particularly, the clip detector assembly 700 includes a grip portion 760 coupled to the detector 730. The grip portion 760 is configured such that a user (e.g., a physician, nurse, etc.) can grip the clip detector assembly 700 and move the clip detector assembly 700 relative to the portion 110 of the patient's body. The grip portion 760 can have a rectangular shape as shown in FIG. 7 or, in other embodiments, can have any other shape or configuration (e.g., curved, square, rectilinear, including indentations or recesses, etc.). In some embodiments, the grip portion 760 is a hollow structure configured to house other components of the clip detector assembly 700 such as control circuitry, communication circuitry, power circuitry, etc. For example, as illustrated in the embodiment of FIG. 7, the clip detector assembly 700 can include a power switch 766 on the grip portion 760 for toggling power to the detector 730 and or other circuitry housed within the grip portion 760. The clip detector assembly 700 can further include a power line 764 coupled to a power source, and an input/output line 762 coupled to external components such as a digital display, speaker, computing device, etc. In certain embodiments, the power line 764 provides about 9 V to the clip detector assembly 700, of which about 5 V are provided to the detector 730. In other embodiments, the detector 730 is provided with about 9 V. In some embodiments, the power line 764 provides about 0.2 A to the detector 730. In some embodiments, the grip portion can include other suitable components and/or connections for facilitating detection of the clip 111.

In certain embodiments, the clip detector assembly 700 can further include a magnetic shield or other component for changing the shape, size, and/or strength of the magnetic field produced by the detector 730. For example, the clip detector assembly 700 can include a shield disposed around the external casing of the detector 730 for directing the magnetic field away from the grip portion 760. In some such embodiments, the shield can prevent, substantially prevent, and/or minimize interference from other metal components (e.g., clamps, scalpels, etc.) that may be used during the detection process and/or a surgical procedure to remove the clip 111.

Figure 8:
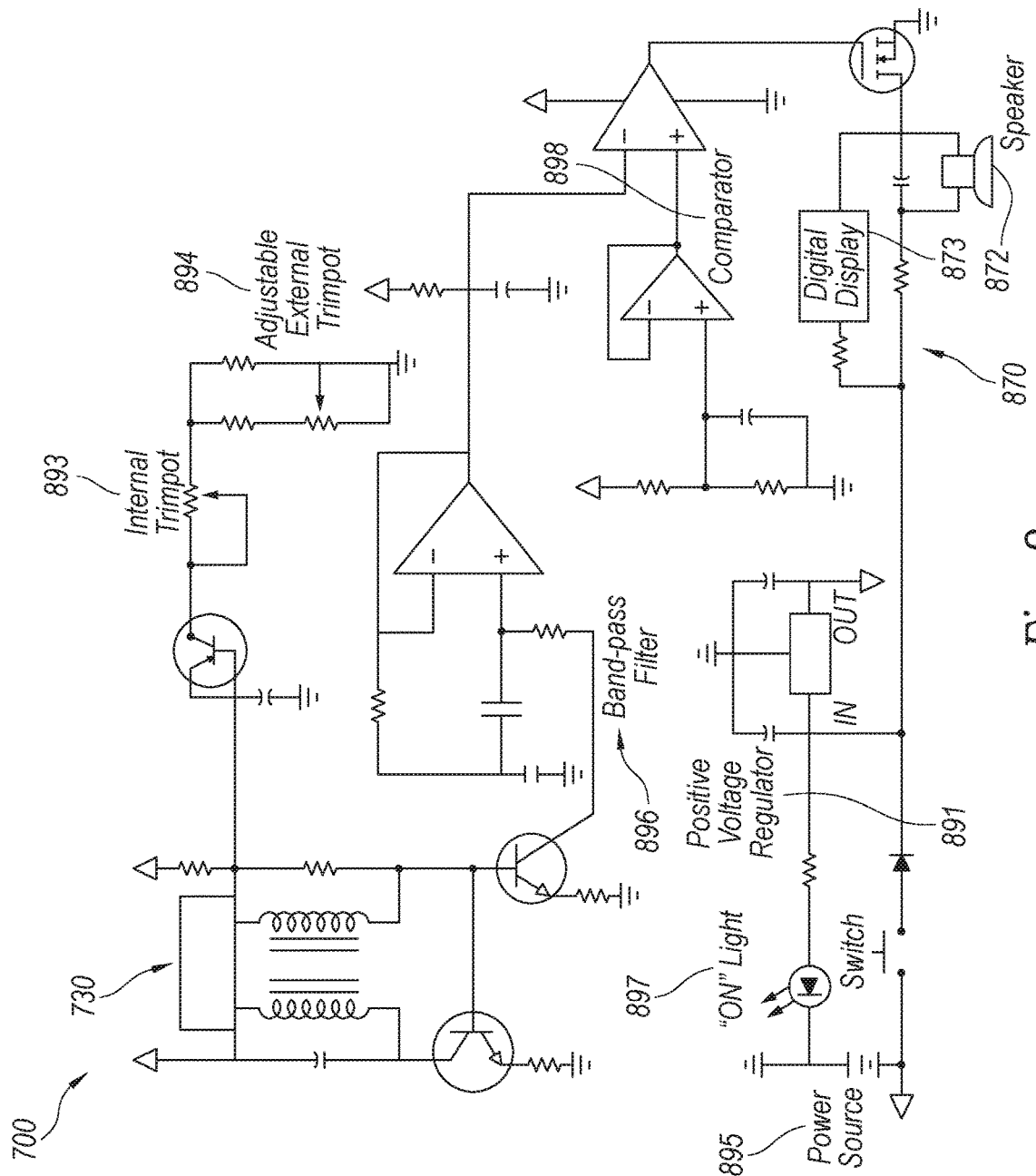
FIG. 8 is a schematic circuit diagram of the clip detector assembly shown in FIG. 7 in accordance with embodiments of the present technology.

FIG. 8 is a schematic circuit diagram of the clip detector assembly 700 in accordance with the present technology. While only the single detector 730 is illustrated in FIG. 8, in other embodiments, multiple detectors (e.g., the detectors 220, 230) may be incorporated into the illustrated circuitry. In some embodiments, the clip detector assembly 700 includes components for adjusting the magnetic field emitted by the transmitting coil of the detector 730. For example, the detector 730 may be adjusted using an internal trimpot 893 and an adjustable external trimpot 894 (collectively, trimpots 893, 894). The trimpots 893, 894 can be used to control resistance in the detector 730, which in turn controls the magnetic field generated by the transmitting coil of the detector 730.

As resistance in the detector 730 decreases, the magnetic field increases, which increases the length of the magnetic field along an axis about which the transmitting and receiving coils extend, but decreases the width of the magnetic field as measured radially from the axis. Conversely, as resistance in the detector 730 increases, the magnetic field decreases, which decreases the length of the magnetic field along an axis about which the transmitting and receiving coils extend, but increases the width of the magnetic field as measured radially from the axis. The internal trimpot 893 may be set during manufacture of the detector 730 in order to account for variations in manufacturing parameters. The adjustable external trimpot 894 may be adjusted by the user of the clip detector assembly 700 during operation. For example, the adjustable external trimpot 894 may be adjusted so as to decrease the magnetic field initially, in order to enable general location identification of the clip 111 while the detector 730 is external to the portion 110 of the patient's body. Once the general location of the clip 111 is determined, the adjustable external trimpot 894 may then be adjusted so as to increase the magnetic field and the detector 730 may be inserted into the portion 110 of the patient's body to determine a more exact location of the clip 111. In certain embodiments, once inserted within the portion 110 of the patient's body, the detector 730 can detect the clip 111 when the detector 730 is within about 1-5 cm (e.g., about 1 cm, 2 cm, 3 cm, etc.) of the clip 111.

In some embodiments, the clip detector assembly 700 may not include the adjustable external trimpot 894 (or any other component for varying the magnetic field generated by the detector 730) and can instead rely on the specific geometry of the detector 730 for providing a magnetic field that permits both general location of the clip 111 while the detector 730 is external to the portion 110 of the patient's body, and determination of a more exact location of the clip 111 after the detector 730 is inserted into the incision 114. Moreover, in some embodiments, the power provided to the detector 730 can be varied (e.g., to the transmitting coil and/or receiving coil of the detector 730) in order to change the shape, size, and/or strength of the magnetic field produced by the detector 730 and/or influence the detection capabilities of the detector 730. Likewise, in some embodiments that employ two detectors (e.g., the detectors 220, 230), the clip detector assembly may not include the adjustable external trimpot 894 and may instead rely on varying geometries of the two detectors to provide different magnetic fields.

The receiving coil of the detector 730 receives the magnetic field generated by the current induced in the metal clip by the transmitting coil of the detector 730, and passes electrical signals to other circuit components of the detector assembly 700. For example, the clip detector assembly 700 can further include a band-pass filter 896 configured to filter out signals that are outside of the range of frequencies that would be produced by the clip 111. The band-pass filter 896 may have, for example, a frequency range within the range of about 1-50 kHz. In some embodiments, the frequency range may be a narrow range of frequencies within about 1-35 kHz of the resonance frequency of the clip 111 (e.g., within about 10 kHz) and/or within about 1% of the resonance frequency of the clip 111. The range may also be defined more narrowly, such as within at most (e.g., less than) about 5 Hz, 10 Hz, 20 Hz, 50 Hz, 100 Hz, or 200 Hz of the resonance frequency of the clip 111. The frequency range may be wide enough to encompass frequencies of multiple types of clips. Accordingly, the band-pass filter 896 may be configured to pass signals from the receiving coil of the detector 730 that are within a frequency range corresponding to the specific clip 111 or clips that are implanted within the portion 110 of the patient's body.

After passing through the band-pass filter 896, the signal is then sent to a comparator 898 that compares the signal to a baseline. The comparator 898 is coupled to a user notification component 870 that is configured to communicate to the user the proximity of the clip 111 to the detector 730. For example, the user notification component 870 can include a speaker 872 and/or a digital display 873. In some embodiments, the speaker 872 is configured to emit a higher pitch or a louder tone (or any sound variation) as the detector 730 is positioned closer to the clip 111. In certain embodiments, the digital display 873 can, for example, display an approximate distance of the clip 111 from the detector 730 and/or display any other indication of the proximity of the clip 111 to the detector 730. As illustrated in the embodiment of FIG. 8, the clip detector assembly 700 can include other components such as, for example, a power source 895, a voltage regulator (e.g., a positive voltage regulator) 891, a power indicator light 897, and/or or other suitable components. Furthermore, any of the circuitry illustrated in FIG. 8 can have digital or analog variants.

Figure 9:
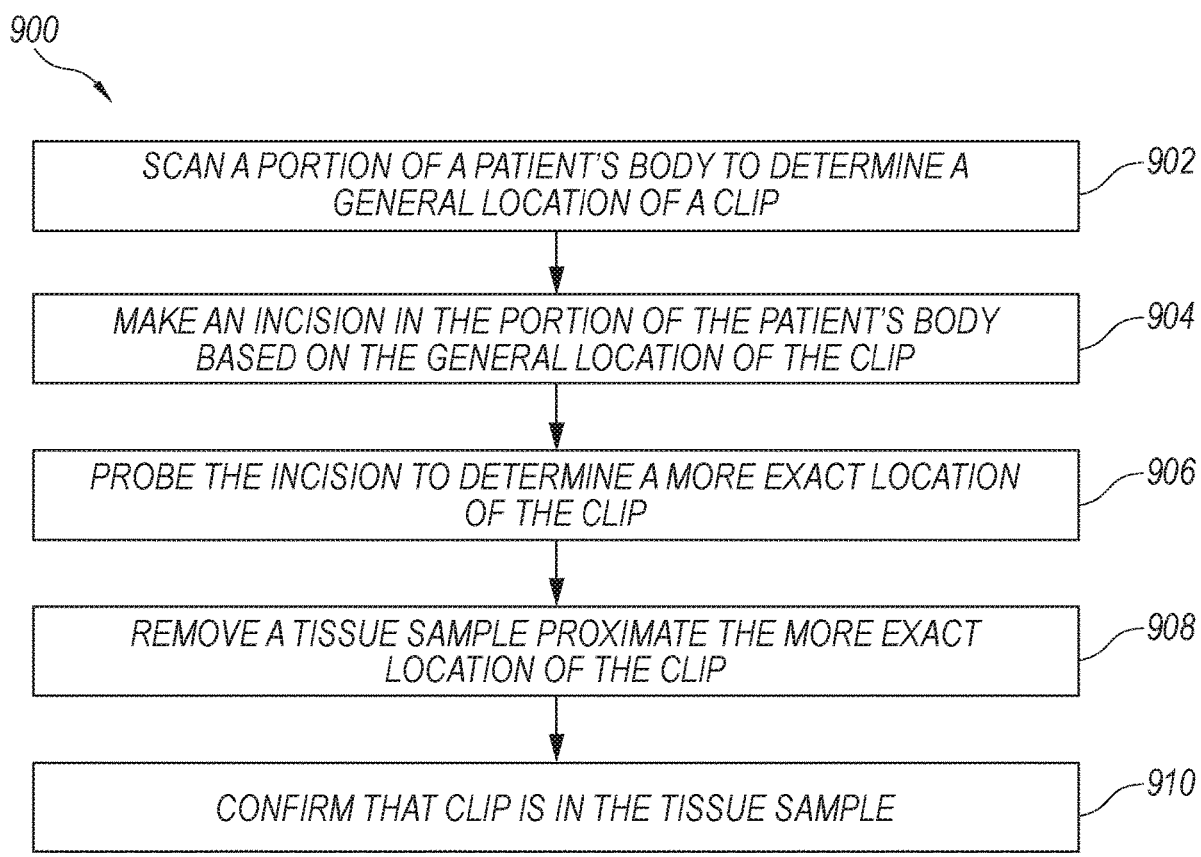
FIG. 9 is a flow diagram of a process for detecting and removing a clip from a portion a patient's body in accordance with embodiments of the present technology.

FIG. 9 is a flow diagram of a process 900 for detecting and removing the clip 111 from the portion 110 of the patient's body in accordance with embodiments of the present technology. The process 900 can be carried out using any of the clip detector assemblies described herein. As described above, prior to the process 900, the clip 111 is inserted into the portion 110 of the patient's body to, for example, mark a biopsy site within the portion 110. In some embodiments, for example, the portion 110 is a breast of the patient and the biopsy site is determined by a mammogram.

Beginning at block 902, the process includes scanning (passing the detector over and/or proximate to) the portion 110 of the patient's body to determine a general location of the clip 111 within the portion 110. For example, a user can pass a detector (e.g., the first detector 220 of FIG. 2, the first detector 620 of FIG. 6, the detector 730 of FIG. 7, etc.) configured to produce a magnetic field capable of inducing an opposing current in the clip 111 at a distance of about 1-20 cm across the skin surface 112 of the portion 110 of the patient's body. The detector and/or other components (e.g., a user notification component) coupled to the detector can alert the user (e.g., via an audio sound) to a general location of the clip 111 within the portion 110.

At block 904, based on the determined general location of the clip 111, the user (or another physician, nurse, etc.) can make the incision 114 in the portion 110 of the patient's body. At block 906, the user can probe the incision with the same detector (e.g., the detector 730) or another detector (e.g., the second detector 230 or the second detector 630) to determine a more exact location of the clip 111. More specifically, the user can insert the detector through the incision 114 and can probe the portion 110 via the incision path 116 to determine the more exact location of the clip 111. In some embodiments, for example, an audio tone or visual readout can alert the user that the detector used to probe the portion 110 is located near and/or becoming nearer to the clip 111. In certain embodiments, the detector can detect the clip 111 when it is positioned within about 3-5 cm of the clip 111.

At block 908, once the more exact location of the clip 111 is determined, a tissue sample surrounding the more exact location may be removed using, for example, a scalpel or cautery. In some embodiments, the tissue sample may include a tumor or other region of interest from the portion 110 of the patient's body, and may include the clip 111 therein. In certain embodiments, at block 910, once the tissue sample is removed, confirmation that the clip 111 was also removed can be made using any of the detectors used to detect the clip 111. In instances where multiple clips 111 are disposed in the portion 110 of the patient's body, some or all of the process 900 may be repeated for each clip 111 to be removed.

As described with reference to FIG. 9, the clip detector assemblies described herein permit clip detection to be carried out in the operating room as part of the same procedure used to remove a tumor or other tissue. In contrast, conventional methods for localizing clips within a patient include surgical localization procedures that are performed as part of a separate procedure and/or outside of the operating room (e.g., in a radiology department). In such conventional surgical localization procedures, a wire, radioactive seed, or reflective device is placed adjacent to the site of the clip to later guide the surgeon to the clip in the operating room. Separating the procedures is inconvenient for the patient and also leads to, among other things: (i) long wait times between the procedures, (ii) patient dissatisfaction from having a wire or other device placed within them, (iii) an increased number of invasive procedures for the patient, and (iv) increased risk to the patient (e.g., from the multiple procedures, from the possibility of a radiative seed breaking, etc.). Requiring a separate surgical localization procedure also places an increased burden on the operating room carrying out the procedures. The present technology reduces the patient pain, risk, and inconvenience inherent in performing a second invasive procedure while also increasing operating room utilization.

EXAMPLES

Several aspects of the present technology are set forth in the following examples.

1. A clip detector assembly for detecting a metal clip within a human patient, the clip detector assembly comprising:
   a detector having
      a ferrous member,
      a transmitting coil positioned radially around a first portion of the ferrous member, wherein the transmitting coil is coupled to a power source and configured to induce a current in the metal clip, and
      a receiving coil positioned radially around a second portion of the ferrous member and configured to (a) receive a magnetic field generated by the current induced in the metal clip and (b) have electrical signals induced therein by the magnetic field;
   a control circuit electrically coupled to the receiving coil, wherein the control circuit is configured to pass the electrical signals from the receiving coil that are within at most 35 kHz of a resonance frequency of the metal clip; and
   a user notification component electrically coupled to the control circuit and configured to receive the electrical signals passed from the control circuit and alert a user to a location of the metal clip.

2. The clip detector assembly of example 1 wherein the control circuit includes a band-pass filter configured to pass the electrical signals from the receiving coil that are within 1% of the resonance frequency of the metal clip.

3. The clip detector assembly of example 1 or 2 wherein the control circuit includes a band-pass filter configured to pass the electrical signals from the receiving coil that are within 10 kHz of the resonance frequency of the metal clip.

4. The clip detector assembly of any one of examples 1-3 wherein the transmitting coil is positioned radially around the receiving coil, and wherein the first portion is substantially the same as the second portion.

5. The clip detector assembly of any one of examples 1-4 wherein the detector includes an outer casing having a diameter less than 25 mm, and wherein the ferrous member, transmitting coil, and receiving coil are positioned within the outer casing.

6. The clip detector assembly of example 5 wherein the outer casing is made of a material that includes at least one of a nylon, PVA, or acrylic.

7. The clip detector assembly of any one of examples 1-6 wherein the transmitting coil is configured to generate a magnetic field, and wherein the detector is adjustable such that the magnetic field can have at least a first strength or a second strength different than the first strength.

8. The clip detector assembly of example 7, further comprising an adjustable trimpot for adjusting the resistance of the transmitting coil.

9. The clip detector assembly of any one of examples 1-8 wherein the user notification component includes at least one of a digital display or a speaker for alerting the user to the location of the metal clip.

10. The clip detector assembly of any one of examples 1-9 wherein the user notification component includes a speaker, wherein the speaker is configured to generate (a) a first sound audible to the user when the detector is at a first location relative to the location of the metal clip and (b) a second sound audible to the user when the detector is at a second location relative to the location of the metal clip, and wherein the second location is different than the first location.

11. The clip detector assembly of any one of examples 1-10 wherein the detector is a first detector, and further comprising:
a second detector having a second ferrous member, a second transmitting coil positioned radially around at least a first portion of the second ferrous member and configured to induce a second current in the metal clip, and a second receiving coil positioned radially around at least a second portion of the second ferrous member and configured to receive a magnetic field generated by the second current induced in the metal clip,
wherein a diameter of the second transmitting coil is less than a diameter of the transmitting coil of the first detector, and wherein a diameter of the second receiving coil is less than a diameter of the receiving coil of the first detector.

12. The clip detector assembly of example 11 wherein the second detector is slidably coupled to the first detector.

13. The clip detector assembly of example 11 or 12 wherein the second detector includes an outer casing having a diameter of less than 25 mm, and wherein the second detector is insertable into a portion of the body of the patient.

14. A method of determining a location of a metal clip inserted within a portion of a body of a human patient, the method comprising:
passing a detector proximate to the portion of the body of the patient while the detector generates a first magnetic field configured to induce a first current in the metal clip;
determining a general location of the metal clip within the portion of the patient based on a second magnetic field generated by the induced first current in the metal clip;
while the detector generates a third magnetic field configured to induce a second current in the metal clip, inserting the detector into the portion of the body of the patient based at least on the determined general location of the metal clip; and
determining the location of the metal clip within the portion of the patient based on a fourth magnetic field generated by the induced second current in the metal clip.

15. The method of example 14 wherein the first and third magnetic fields have the same size, shape, and/or strength.

16. The method of example 14 or 15 wherein e first and third magnetic fields have a different size, shape, and/or strength.

17. The method of any one of examples 14-16 wherein, while passing the detector proximate to and/or inserting the detector into the portion of the body of the patient, a user notification component coupled to the detector guides a user toward the metal clip.

18. The method of any one of examples 14-17 wherein:
determining the general location of the metal clip based on the second magnetic field includes receiving first signals from the detector based on the second magnetic field and passing the first signals to a user notification component only when the first signals are within at most 35 kHz of a resonance frequency of the metal clip,
determining the location of the metal clip based on the fourth magnetic field includes receiving second signals from the detector based on the fourth magnetic field and passing the second signals to the user notification component only when the second signals are within at most 35 kHz of the resonance frequency of the metal clip, and
the user notification component guides a user toward the metal clip.

19. A system for detecting a metal clip disposed within a portion of a body of a patient, the system comprising:
a detector having an outer casing with a diameter less than 25 mm, wherein the detector is configured to generate (a) a first magnetic field when the detector is positioned external to the portion of the body of the patient and (b) a second magnetic field when the detector is inserted into the portion of the body of the patient, wherein the first magnetic field induces a first current in the metal clip, and wherein the second magnetic field induces a second current in the metal clip;
a control circuit coupled to the detector and configured to receive first signals induced in the detector by a third magnetic field generated by the induced first current in the metal clip,
receive second signals induced in the detector by a fourth magnetic field generated by the induced second current in the metal clip, and
pass first and second signals that are within 1% of a resonance frequency of the metal clip; and
a user notification component configured to receive the passed first and second signals from the control circuit and alert a user to a location of the metal clip within the portion of the body of the patient.

20. The system of example 19 wherein at least one of a size, shape, or strength of the first magnetic field is different from a size, shape, or strength of the second magnetic field.

Conclusion

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. Moreover, the various embodiments described herein may also be combined to provide further embodiments. For example, the disclosed clip detector assemblies may include one, two, or more detectors, and may include some or all of the circuit elements described with reference to FIGS. 5 and 8.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms may also include the plural or singular term, respectively. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A clip detector assembly for detecting a metal clip within a human patient, the clip detector comprising:
    a first detector having—
        a first ferrous member,
        a first transmitting coil positioned radially around a first portion of the first ferrous member, wherein the first transmitting coil is coupled to a power source and configured to induce a first current in the metal clip, and
        a first receiving coil positioned radially around a second portion of the first ferrous member and configured to (a) receive a first magnetic field generated by the first current induced in the metal clip and (b) have electrical signals induced therein by the first magnetic field;
    a second detector slidably coupled to the first detector, the second detector having—
        a second ferrous member;
        a second transmitting coil positioned radially around at least a first portion of the second ferrous member and configured to induce a second current in the metal clip, wherein a diameter of the second transmitting coil is less than a diameter of the first transmitting coil; and
        a second receiving coil positioned radially around at least a second portion of the second ferrous member and configured to receive a second magnetic field generated by the second current induced in the metal clip, wherein a diameter of the second receiving coil is less than a diameter of the first receiving coil;
    a control circuit electrically coupled to the first receiving coil, wherein the control circuit is configured to pass the electrical signals from the first receiving coil that are within at most 35 kHz of a resonance frequency of the metal clip; and
    a user notification component electrically coupled to the control circuit and configured to receive the electrical signals passed from the control circuit and alert a user to a location of the metal clip.

2. The clip detector assembly of claim 1 wherein the control circuit includes a band-pass filter configured to pass the electrical signals from the first receiving coil that are within 1% of the resonance frequency of the metal clip.

3. The clip detector assembly of claim 1 wherein the control circuit includes a band-pass filter configured to pass the electrical signals from the first receiving coil that are within 10 kHz of the resonance frequency of the metal clip.

4. The clip detector assembly of claim 1 wherein the first transmitting coil is positioned radially around the first receiving coil, and wherein the first portion of the first ferrous member is substantially the same as the second portion of the first ferrous member.

5. The clip detector assembly of claim 1 wherein the first detector includes an outer casing having a diameter less than 25 mm, and wherein the first ferrous member, the first transmitting coil, and the first receiving coil are positioned within the outer casing.

6. The clip detector assembly of claim 5 wherein the outer casing is made of a material that includes at least one of a nylon, polyvinyl alcohol (PVA), or acrylic.

7. The clip detector assembly of claim 1 wherein the first transmitting coil is configured to generate a magnetic field, and wherein the first detector is adjustable such that the magnetic field generated by the first transmitting coil can have at least a first strength and a second strength different than the first strength.

8. The clip detector assembly of claim 7, further comprising an adjustable trimpot for adjusting a resistance of the first transmitting coil.

9. The clip detector assembly of claim 1 wherein the user notification component includes at least one of a digital display or a speaker for alerting the user to the location of the metal clip.

10. The clip detector assembly of claim 1 wherein the user notification component includes a speaker, wherein the speaker is configured to generate (a) a first sound audible to the user when the first detector is at a first location relative to the location of the metal clip and (b) a second sound audible to the user when the first detector is at a second location relative to the location of the metal clip, and wherein the second location is different than the first location.

11. The clip detector assembly of claim 1 wherein the second detector includes an outer casing having a diameter of less than 25 mm, and wherein the second detector is insertable into a portion of the body of the patient.

* * * * *

UNITED STATES PATENT AND TRADEMARK OFFICE
CERTIFICATE OF CORRECTION

PATENT NO. : 11,253,167 B2  
APPLICATION NO. : 16/328430  
DATED : February 22, 2022  
INVENTOR(S) : DeMore et al.

Page 1 of 1

It is certified that error appears in the above-identified patent and that said Letters Patent is hereby corrected as shown below:

In the Specification

In Column 4, Line 11, delete "casing" and insert -- casing 221 --.

In Column 5, Line 63, delete "etc." and insert -- etc.). --.

In Column 6, Line 18, delete "e.g.," and insert -- (e.g., --.

In Column 6, Line 28, delete "about" and insert -- (e.g., about --.

In Column 7, Line 40, delete "550" and insert -- 550, --.

In Column 9, Line 16, delete "and or" and insert -- and/or --.

In Column 10, Line 15, delete "III." and insert -- 111. --.

In Column 11, Line 23, delete "(passing" and insert -- (e.g., passing --.

In Column 14, Line 1, delete "e" and insert -- the --.

In Column 14, Line 36, delete "to" and insert -- to— --.

Signed and Sealed this  
Twenty-seventh Day of September, 2022

Katherine Kelly Vidal  
*Director of the United States Patent and Trademark Office*